United States Patent [19]

Seri et al.

[11] Patent Number: 5,811,077
[45] Date of Patent: Sep. 22, 1998

[54] METHOD OF NMR IMAGING

[75] Inventors: Shigemi Seri; Makoto Azuma; Kumiko Iwai, all of Chiba, Japan

[73] Assignee: Nihon Medi-Physics Co., Ltd., Hyogo, Japan

[21] Appl. No.: 768,613

[22] Filed: Dec. 18, 1996

Related U.S. Application Data

[62] Division of Ser. No. 775,891, Oct. 15, 1993, abandoned.

[30] Foreign Application Priority Data

Oct. 16, 1990 [JP] Japan ................................. 2-278661

[51] Int. Cl.$^6$ .......................... A61K 49/04; A61K 49/00; C07D 257/02
[52] U.S. Cl. ....................... 424/9.363; 514/184; 540/465; 556/1
[58] Field of Search ........................ 424/9.363; 514/184; 534/16; 540/465; 556/1

[56] References Cited

U.S. PATENT DOCUMENTS

| | | | |
|---|---|---|---|
| 4,639,365 | 1/1987 | Sherry | 424/9 |
| 4,880,008 | 11/1989 | Lauffler | 128/653.4 |
| 4,899,755 | 2/1990 | Lauffler | 128/654 |
| 4,963,344 | 10/1990 | Gries et al. | 429/9 |
| 4,983,376 | 1/1991 | Sherry | 540/465 |

FOREIGN PATENT DOCUMENTS

| | | |
|---|---|---|
| WO 8602352 | 4/1986 | WIPO . |
| WO 8606605 | 11/1986 | WIPO . |
| 8911475 | 11/1989 | WIPO .................... 540/465 |

OTHER PUBLICATIONS

Brittain et al. Inorg. Chem. 23(26), pp. 4459–4466, 1984.
Bosquet, J–C., et al, Radiology, vol. 166, 693–698 (1988).
Kilgore, D.P., Radiology, vol. 160, 757–761 (1986).
Knop, F.H., et al, Journal of Computer Assisted Tomography 11 (10:35–42, Jan./Feb. 1987.
Desreux, J.F., et al, Nucl. Med. Biol. vol. 15, No. 1, pp. 9–15, 1988.
Brittain, H.G., et al, Chemical Abstracts 102:14419e, 1985.
Wedeking, P., et al., "Biodistribution and Excretion of New Gd–Complexes in Mice," Book of Abstracts, vol. 2, p. 801, Society of Magnetic Resonance in Medicine, 8th Annual Meeting (1989).

*Primary Examiner*—Yogendra N. Gupta

[57] ABSTRACT

A gadolinium complex of 1,4,7,10-tetraazacyclododecane-1,4,7,10-$\alpha,\alpha',\alpha'',\alpha'''$-tetrakis(methylacetic acid) or its salt, which is useful as a nuclear magnetic resonance imaging agent.

15 Claims, 3 Drawing Sheets

METHOD OF NMR IMAGING

This application is a division of application Ser. No. 07/775,891, filed Oct. 15, 1991, abandoned.

The present invention relates to a magnetic resonance imaging agent. More particularly, it relates to a gadolinium (hereinafter referred to as "Gd") complex and its use as a nuclear magnetic resonance (MR) imaging agent.

Of paramagnetic ions, Gd ion has a strong relaxation property and is advantageously used for MR imaging. Since, however, it frequently produces a considerable toxicity at such a concentration as required for MR imaging, utmost care must be paid on its administration to a living body. Gd ion is therefore normally employed as a complex coordinated with a suitable chelating agent. While there are reported various Gd complexes, the dimeglumine salt of the Gd complex of diethylenetriaminepentaacetic acid (Gd-DTPA) is the only complex as presently available on the market (H. J. Weinmann et al: Am. J. Roentgenology, 142, 619–624 and 625–630 (1984)). Gd-DTPA or its salt has a stability constant of $10^{17}$ at a physiological pH and is still not sufficiently acceptable to a living body (C. F. Meares et al: Can. Res. (Suppl.), 50, 789s–793s (1990)).

As a result of the extensive study, it has been found that a Gd complex of 1,4,7,10-tetraazacyclododecane-1,4,7,10-α,α',α",α'''-tetrakis(methylacetic acid) (hereinafter referred to as "Gd-DOTMA") or its salt shows a significantly higher stability constant of complex than Gd-DTPA or its salt. Thus, Gd-DOTMA or its salt is more stable and less toxic than Gd-DTPA or its salt. It has also been found that Gd-DOTMA or its salt has a relatively strong contrast enhancement and can be used advantageously as an MR imaging agent. This invention is based on the above findings.

Accordingly, a main object of the present invention is to provide a chemically stable Gd complex, of which the stability constant of complex at a physiological pH is suppressed to a possible minimum degree and which is useful as an MR imaging agent with high safety to a living body.

The Gd complex of the invention may be a Gd complex of DOTMA or its salt. Gd to be complexed with DOTMA may be Gd itself or its compound such as chloride and oxide.

DOTMA can be synthesized in a conventional method, for instance, by reacting 1,4,7,10-tetraazacyclododecane with 2-halopropionic acid according to the following scheme (J. F. Desreux et al: Inorg. Chem., 23, 4459–4466 (1984)):

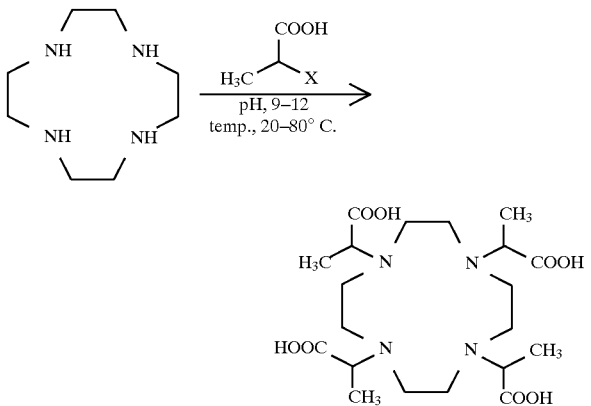

wherein X is halogen (e.g. chlorine, bromine).

In the above reaction, 2-halopropionic acid may take any optically active or inactive form. It is also possible to use 2-halopropionate ester. When 2-halopropionate ester is used, however, saponification must be carried out after the above reaction.

Production of Gd-DOTMA may be also accomplished by a conventional method. For example, when the Gd compound is used in the form of hydrochloride, the reaction proceeds as follows:

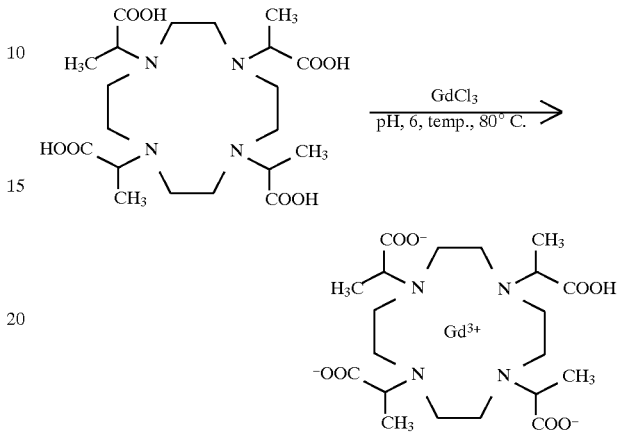

The Gd complex of the invention covers any neutral salt comprising a physiologically acceptable organic or inorganic cation as a counter-ion. Gd-DOTMA has one free acid group, and its neutralization with a counter-ion increases the solubility and decreases the osmotic pressure, whereby its applicability to a living body is advantageous. Examples of the counter-ion are those originated from sodium, potassium, lithium, lysine, arginine, ornithine, meglumine, diethanolamine, etc.

The representative Gd complex according to the invention has the following formula:

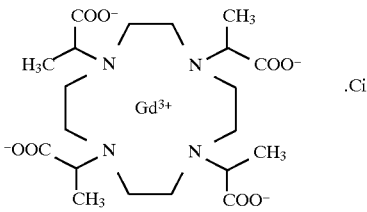

wherein Ci is an organic or inorganic cation as a counter-ion.

As is clear from the above formula, four asymmetric carbon atoms are present in the DOTMA molecule, and their optical rotations may be optionally selected. The above formula covers any steric configuration.

The Gd complex of the invention may be admixed with any pharmaceutically acceptable carrier or diluent to prepare an MR imaging agent in any appropriate preparation form. While no specific limitation is present on the preparation form, the MR imaging agent is preferred to be in an aqueous solution, particularly in a physiologically acceptable aqueous solution so as to make intravenously injectionable.

Gd-DOTMA or its salt as the essential component in the MR imaging agent of the invention has, at a physiological pH, a stability constant significantly higher than that of the Gd complex of 1,4,7,10-tetraazacyclododecane-N,N',N", N'''-tetraacetic acid (Gd-DOTA), which has so far been acknowledged as the most stable Gd complex (C. F. Meares et al: Can. Res. (Suppl.), 50, 789s–793s (1990)). Such a high stability constant assures a high in vivo stability, and the in vivo toxicity due to Gd ion is much lowered. In fact, a minimal lethal dose of Gd-DOTMA in mice is higher than a lethal dose 50 ($LD_{50}$) of Gd-DTPA.

Also, Gd-DOTMA or its salt provides an enchanced imaging effect in an MR imaging apparatus with a magnetic strength (0.5 to 2 T) as conventionally used than Gd-DTPA or its salt. Accordingly, it is advantageous to use Gd-DOTMA or its salt instead of Gd-DTPA or its salt, since the former achieves substantially the same imaging effect as the latter at a lower dose and the production of the toxicity is much suppressed. Conversely, so long as the same dose is used, Gd-DOTMA or its salt affords much more information than Gd-DTPA or its salt does, which leads to enhancement of its clinical utility. As apparent in Test Examples which will hereinafter follow, the imaging effect of Gd-DOTMA or its salt is superior to that as obtained by Gd-DTPA or its salt.

Further, since $^{153}$Gd-DOTMA is rapidly excreted into urine (W. C. Eckelman et al: The 8th SMRM, Abstract, 801 (1989)), the biodistribution pattern of Gd-DOTMA or its salt may be considered to be identical to that of a urinary-blood vessel imaging agent as used in X-ray diagnosis. Yet, it should be noted that said Abstract discloses only the distribution of $^{153}$Gd-DOTMA in mice and is entirely silent on its use as an MR imaging agent.

After all, Gd-DOTMA or its salt is low in the in vivo toxicity and yet shows a strong imaging effect. Accordingly, an MR imaging agent comprising Gd-DOTMA or its salt is quite advantageous.

Practical and preferred embodiments of the present invention are explained in detail in the following Reference Examples, Examples and Test Examples, to which the invention is not limited in any way.

REFERENCE EXAMPLE 1

Preparation of DOTMA 1,4,7,10-Tetraazacyclododecane tetrahydrochloride (2.639 g; 8.29 mmol) was neutralized, and (S)-2-chloropropionic acid (8.65 g; 79.0 mmol) neutralized under ice-cooling was gradually added thereto, followed by stirring in a water bath of 50° C. for 18 hours. To the resultant mixture, (S)-2-chloropropionic acid (3.946 g; 36.4 mmol) was added, and stirring was continued in the same bath for 30 hours, during which the pH was kept at 9 to 10. The reaction mixture was cooled to room temperature and adjusted to pH 11 with addition of aqueous sodium hydroxide solution. Precipitated crystals were collected by filtration, dissolved in water and made acidic (pH, 2) with addition of hydrochloric acid, followed by concentration. Crude crystals thus obtained were recrystallized from ethanol and water (1:1) to give DOTMA in the form of hydrochloride (2.982 g, yield, 63%).

$^1$H-NMR spectrum ($D_2O$, ppm/TMS): 1.3 (d, 12 H), 2.8 (bs, 8 H), 3.1 (bs, 8 H), 3.6 (q, 4 H).

FAB-mass spectrum (anion, m/z):459 [(M−H)$^-$].

Elementary analysis for $C_{20}H_{45}N_4O_{12}Cl$ (%): Calcd.: C, 42.2; H, 8.0; N, 9.8; Cl, 6.2. Found: C, 41,6; H, 8.9; N, 9.8; Cl, 7.1.

EXAMPLE 1

Preparation of Gd-DOTMA

DOTMA.HCl (1.60 g; 3.2 mmol) was dissolved in an appropriate amount of water, and gadolinium chloride hexahydrate (1.43 g; 3.8 mmol) was added thereto. The mixture was transferred to a water bath of 80° C. and adjusted to pH 6, followed by stirring for 3 hours. The reaction mixture was cooled to room temperature and concentrated. The residue was combined wiht an appropriate amount of water, and insoluble materials were removed by filtraton. The filtrate was purified by cation exchange resin chromatography (resin: AG50W-X4, eluting solvent: water) to give Gd-DOTMA (2.06 g, yield, 30%).

FAB-mass spectrum (anion, m/z):614 [(M−H)$^-$].

Elementary analysis for $C_{20}H_{41}N_4O_{12}Gd$ (%): Calcd.: C, 35.0; H, 6.0; N, 8.2; Gd, 22.9. Found: C, 34.7; H, 6.5; N, 8.1; Gd, 22.8.

EXAMPLE 2

Preparation of Gd-DOTMA Dimeglumine Salt

Gd-DOTMA (0.247 g; 0.35 mmol) obtained in Example 1 was dissolved in water (0.7 ml), and meglumine (0.137 g; 0.70 mmol) was added thereto to give a pale yellow solution of Gd-DOTMA dimeglumine salt (concentration, 0.5 mol/l; pH, about 7).

Gd concentration (ICP spectrometry) (per 1 ml):
Calcd.: 39.25 mg. Found: 37.50 mg.

TEST EXAMPLE 1

Measurement of Stability Constant of Complex (Chelation Stability Constant) on Gd-DOTMA DOTMA.HCl (31.2 mg; 0.06 mmol) was dissolved in water (0.5 ml), and aqueous $^{153}$GdCl$_3$ solution (0.2 ml, 2.2 MBq) and a solution of gadolinium chloride hexahydrate (27.3 mg; 0.073 mmol) in water (0.5 ml) were added. The mixture was adjusted to pH 6 with addition of 1N aqueous sodium hydroxide solution and allowed to react at 80° C. for 3 hours. The reaction mixture was purified by cation exchange resin chromatography (resin: AG50W-X4, eluting solution: water) and concentrated. The residue was dissolved in ethanol, and insoluble materials were filtered off, and the filtrate was concentrated to give $^{153}$Gd-DOTMA containing Gd-DOTMA (13.93 mg; yield, 38%).

The thus obtained $^{153}$Gd-DOTMA containing Gd-DOTMA (6.43 mg; 0.01 mmol) was dissolved in 0.1M aqueous potassium nitrate solution (2.0 ml), and DOTA (4.19 mg; 0.01 mmol) in 0.1M aqueous potassium nitrate solution (1.0 ml) was added thereto. The resultant mixture was neutralized with addition of an appropriate amount of 1N sodium hydroxide and subjected to incubation at 80° C. for 910 hours. The Gd-DOTMA and Gd-DOTA ratio in the reaction mixture was measured on the basis of the radioactivity concentration by thin layer chromatography (thin layer: silica gel 60; developing solvent: ethyl acetate/methanol/aqueous ammonia=2/2/1).

The amounts of Gd-DOTMA and Gd-DOTM in the mixture were respectively 98.8% and 1.2%, from which the stability constant of Gd-DOTMA was calculated and shown in Table 1 below:

TABLE 1

| Complex | Stability constant (pH, 7) |
|---|---|
| Gd-DOTMA | $10^{26}$ |
| Gd-DOTA | $10^{22}$*) |
| GD-DTPA | $10^{17}$*) |

*)C.F. Meares et al: Can.Res.(Suppl.), 50, 789s–793s (1990)

TEST EXAMPLE 2

Acute Toxicity of Gd-DOTMA Dimeglumine Salt

ICR strain female mice each weighing 30.8±1.4 g (8-weeks old; 5 animals/group) were intravenously injected with 6 mmol/kg of Gd-DOTMA dimeglumine salt (0.5 M) obtained in Example 2. Observation was made on the death for 14 days after the injection to determine a minimum lethal dose (MLD). For comparison, the MLD value was also determined on Gd-DTPA dimeglumine salt in mice injected with the Gd-DTPA in the same manner as above. The results are shown in Table 2.

TABLE 2

| Complex salt | MLD (mmol/kg) |
|---|---|
| Gd-DOTMA dimeglumine salt | more than 6 |
| Gd-DTPA dimeglumine salt | more than 4.8 |

TEST EXAMPLE 3

Relaxation of Gd-DOTMA

Gd-DOTMA obtained in Example 1 was dissolved in deionized water, and the proton relaxation time ($T_1$ and $T_2$, msec) at 39° C. for this complex solution at different concentrations was measured on NMR spectrometer at 6.36 T (JEOL, LTD.). The results are shown in Table 3.

TABLE 3

| Concentration (mM) | $T_1$ (msec) | $T_2$ (msec) |
|---|---|---|
| 4.7 | 76 | 60 |
| 2.4 | 164 | 127 |
| 0.5 | 711 | 571 |
| 0 | 4393 | 1420 |

It is understood from the above results that Gd-DOTMA at a concentration of 4.7 mM shortened the $T_1$ relaxation time of water about 58 times and the $T_2$ relaxation time about 24 times.

On the basis of the results in Table 3, the relaxation degrees ($R_1$ and $R_2$, $(mM \cdot S)^{-1}$) on the $T_1$ and $T_2$ were calculated, and the results are shown in Table 4.

TABLE 4

| Compound | $R_1$ $(mM \cdot S)^{-1}$ | $R_2$ $(mM \cdot S)^-$ |
|---|---|---|
| Gd-DOTMA | 2.7 | 3.4 |
| Gd-DTPA | 2.9 | 3.7 |

As understood from the above, Gd-DOTMA shows a good in vitro relaxation effect, which is nearly equal to that of Gd-DTPA measured in the same manner. Thus, Gd-DOTMA is effective as an imaging agent.

TEST EXAMPLE 4

Apparent Relaxation Degree Measured by a Phantom System

As the phantom system, there was used a cylindrical plastic bottle filled with water, in which an MR tube was fixed. An aqueous solution of Gd-DOTMA dimeglumine salt at a concentration of 0.05, 0.1, 0.2, 0.5, 1.0, 2.5 or 5.0 mM was filled into the MR tube and sealed, and imaging was performed by a spin echo technique with a repetition time (TR) of 600, 1000, 1500, 2000 or 2400 msec and an echo time (TE) of 30 or 100 msec. From the signal intensity, the apparent relaxation degree was calculated. In the same manner, imaging was performed using Gd-DTPA dimeglumine salt.

For imaging, CSI omega (General Electric) was used, and the following conditions were adopted: magnetic field intensity, 2 T; imaging coil, 6 cmØ bird-cage type coil; spin echo technique with slice thickness of 4 mm and resolving power of 256×128.

The apparent relaxation degree ($R'_1$ or $R'_2$, $((mM \cdot S)^{-1})$ calculated from the signal intensity is shown in Table 5.

TABLE 5

| Compound | $R_1'$ $(mM \cdot S)^{-1}$ | $R_2$ $(mM \cdot S)^-$ |
|---|---|---|
| Gd-DOTMA | 3.4 | 4.8 |
| Gd-DTPA | 1.8 | 2.4 |

Gd-DOTMA shows a good relaxation, which is about 1.8 times that of Gd-DTPA. Thus, Gd-DOTMA provides unexpectedly a stronger imaging effect than Gd-DTPA.

TEST EXAMPLE 5

Relaxation Effect of Gd-DOTMA on Blood and Organs in Rat (Ex Vivo Study)

SD strain female rats each weighing 197 g or 202 g (11-weeks old) were anesthetized with thiopental, and an aqueous solution (0.5M) of Gd-DOTMA dimeglumine salt was injected into a tail vein at a dose of 0.1 mmol/kg. About 5 minutes thereafter, the animals were sacrificed, and the relaxation time ($T_1$ and $T_2$, msec) was measured on blood, heart, kidney and liver at room temperature by the use of NMR 6.35 T (JEOL, LTD.).

As the control, SD strain female rats each weighing 200 g (11-weeks old) were anesthetized with thiopental, sacrificed and subjected to measurement of the relaxation time in the same manner as above. The results are shown in Tables 6 and 7.

TABLE 6

| Organ | Control rat $T_1$ (msec) | Treated rat $T_1$ (msec) |
|---|---|---|
| Blood | 1843 | 750 |
| Heart | 1635 | 1140 |
| Kidney | 1478 | 350 |
| Liver | 966 | 630 |

TABLE 7

| Organ | Control rat $T_2$ (msec) | Treated rat $T_2$ (msec) |
|---|---|---|
| Blood | 70 | 55 |
| Heart | 36 | 33 |
| Kidney | 41 | 31 |
| Liver | 19 | 18 |

In comparison with the relaxation time in the control animals, the relaxation time in the treated animals could be shortened effectively, for instance, about 2.5 times in blood and about 4 times in kidney.

TEST EXAMPLE 6

Imaging Effect of Gd-DOTMA Dimeglumine Salt on Rat Heart (In Vivo Study)

Thiopental-anesthetized SD strain female rats each weighing 198 g (9-weeks old) were fixed in the magnetic field in an MRI apparatus and injected with an aqueous solution of Gd-DOTMA dimeglumine salt (0.5M) at a dose of 0.2 mmol/kg through a cannula fixed at the femoral vein. After about 0.5 minute, the animals were killed by administration of an aqueous solution of pentobartital through the cannula, and MR measurement (longitudinal view) of the chest region including the heart was performed.

As the control, SD strain female rats each weighing 186 g (9-weeks old) were killed with administration of an aqueous solution of pentabarbital and subjected to MR measurement.

Imaging was performed using CSI Omega (General Electric) under the following conditions: magnetic field intensity, 2 T; imaging coil, 6 cmØ bird-cage type coil; spin echo technique with a slice thickness of 4 mm and a resolving power of 256×256; $T_1$ weighted (TR/TE, 600/30 msec).

FIG. 1 in the accompanied drawings is an MR image showing a sectional view of the chest region including the heart in a normal rat.

FIG. 2 is an MR image showing a sectional view of the chest region including the heart in a rat given Gd-DOTMA dimeglumine salt.

The Gd-DOTMA dimeglumine salt enhanced significantly the signal intensity in cardiac pool and lungs as well as their related blood vessels and gave a clear contrast with cardiomuscules. Thus, Gd-DOTMA dimeglumine salt would be distributed promptly to the blood circulation system and give a strongly enhanced signal in these regions.

TEST EXAMPLE 7

Contrast Enhancement of Gd-DOTMA Dimeglumine Salt on Rat Kidneys (In Vivo Study)

Thiopental-anesthetized SD strain female rats each weighing 184 g (9-weeks old) were pronely fixed in the magnetic field in an MRI apparatus and given an aqueous solution of Gd-DOTMA dimeglumine salt (0.5M) at a dose of 0.5 mmol/kg through a cannula fixed at the femoral vein. After 30 minutes, MR measurement (longitudinal view) of the adbominal region including the kidneys was performed.

As the control, the animals were subjected to imaging of the same part prior to administration of Gd-DOTMA dimeglumine salt.

Imaging was performed at the same conditions as in Test Example 6.

Gd-DOTMA dimeglumine salt is promptly excreted into urine through the blood circulation system and the kidneys. The signal intensity in the kidneys is increased by the administration of Gd-DOTMA dimeglumine salt and becomes nearly equal to that in the surrounding fat tissue. In this instance, the signal intensity in said region of the kidney (i.e. around the enpelvis renalis at the left kidney) after the administration is increased two times that before the administration. The micro-structure in the kidney is imaged very well.

TEST EXAMPLE 8

Contrast Enhancement of Gd-DOTMA Dimeglumine Salt on Rat Urinary System (In Vivo Study)

Thiopental-anesthetized SD strain female rats each weighing 195 g (13-weeks old) were pronely fixed in the magnetic field in an MRI apparatus and given an aqueous solution of Gd-DOTMA dimeglumine salt (0.5M) at a dose of 0.1 mmol/kg through a cannula fixed at the femoral vein, and MR image (longitudinal view) of the abdominal region including the bladder was acquired 125 minutes after the administration. As the control, the animals were subjected to imaging of the same region prior to administration.

Imaging was performed at the same conditions as in Test Example 6.

Figure 1:
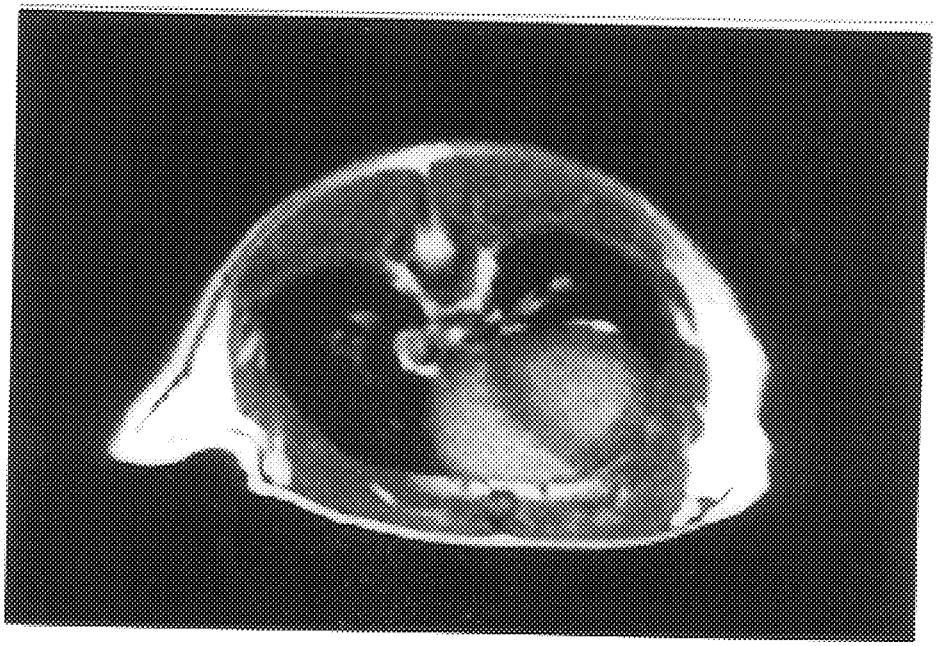
Figure 2:
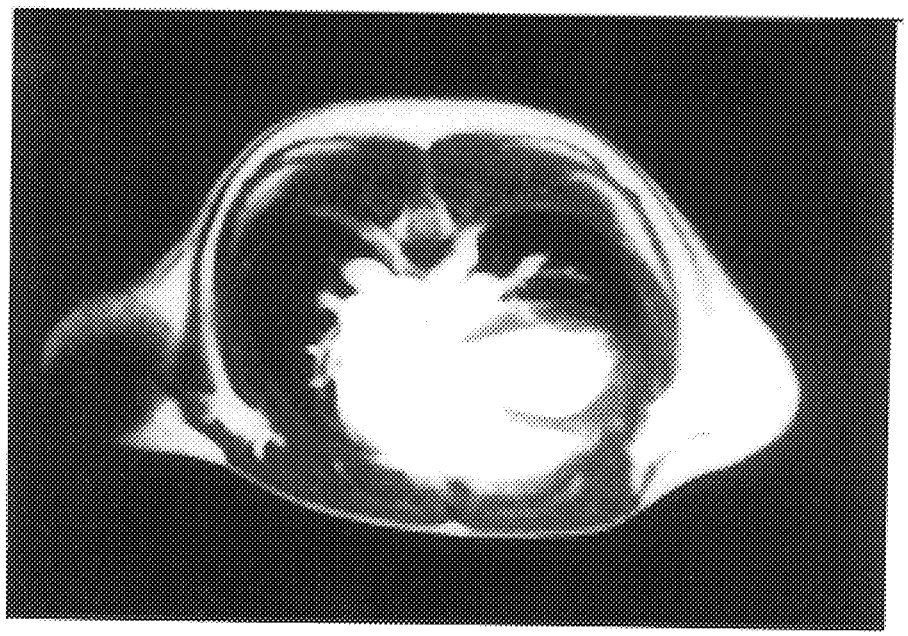
Figure 3:
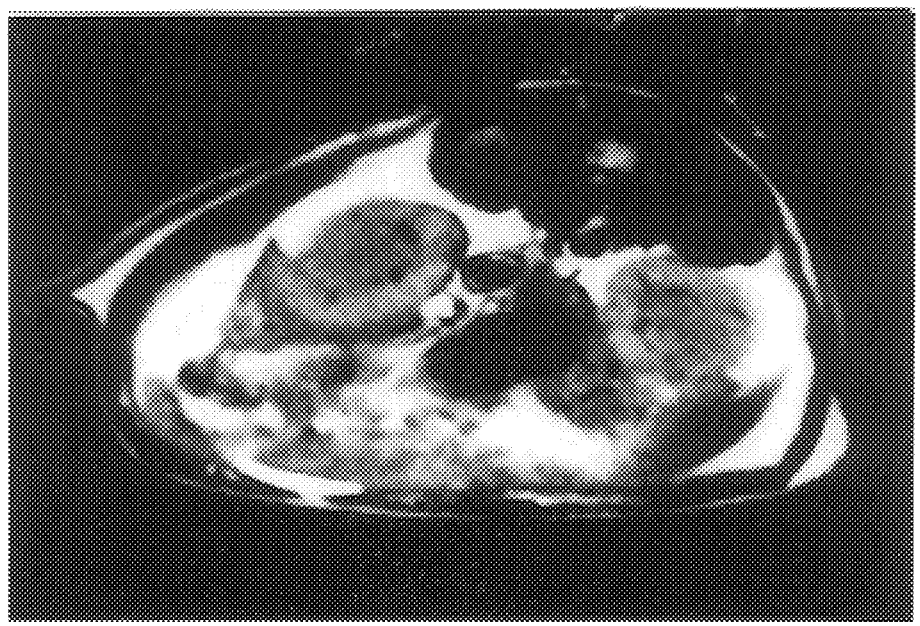
FIG. 3 is an MR image showing a sectional view of the abdominal region including the kidneys prior to administration. The kidneys were slightly imaged as the low intensity area enclosed with a fat tissue of high signal intensity.
Figure 4:
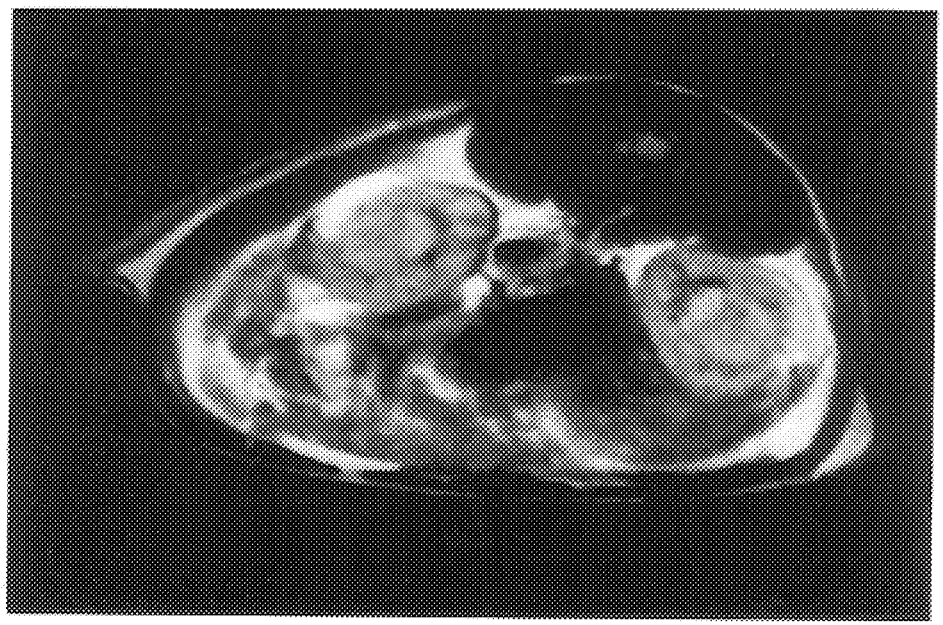
FIG. 4 is an MR image showing a sectional view of the abdominal region including the kidneys 30 minutes after administration of Gd-DOTMA dimeglumine salt.
Figure 5:
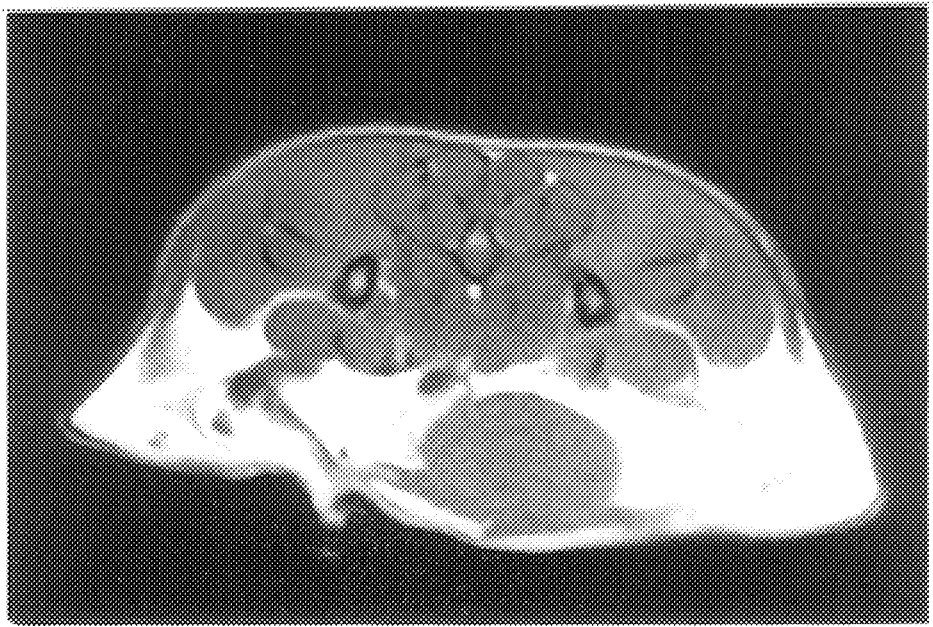

FIG. 5 is an MR image showing a sectional view of the abdominal region including the bladder prior to administration.

Figure 6:

FIG. 6 is an MR image showing a sectional view of the abdominal region including the bladder 125 minutes after the administration with Gd-DOTMA dimeglumine salt. Elimination of the complex by renal excretion to the ladder is clearly imaged.

What is claimed is:

1. A method of enhancing NMR imageability of a patient comprising administering to the patient an amount effective to enhance NMR image contrast, of a nuclear magnetic resonance imaging agent which comprises gadolinium complex of 1,4,7,10-tetraazacyclododecane-1,4,7,10-α,α',α",α'''-tetrakis(methylacetic acid), or its salt, and a pharmaceutically acceptable inert carrier or diluent.

2. The method of claim 1 wherein the gadolinium complex of 1,4,7,10-tetraazacyclododecane-1,4,7,10-α,α',α", α'''-tetrakis(methylacetic acid) is in its salt form originated from sodium, potassium, lithium, lysine, arginine, ornithine, meglumine or diethanolamine.

3. The method of claim 2 wherein gadolinium complex of 1,4,7,10-tetraazacyclododecane-1,4,7,10-α,α',α",α'''-tetrakis(methylacetic acid) is in its salt form and is dissolved in a physiologically acceptable aqueous solution.

4. The method of claim 3 wherein the gadolinium complex of 1,4,7,10-tetraazacyclododecane-1,4,7,10-α,α',α", α'''-tetrakis(methylacetic acid) is in its salt form and is present in the nuclear magnetic resonance imaging agent in a concentration of $1 \times 10^{-5}$ to $1 \times 10$ mol/l.

5. The method of claim 1 wherein the nuclear magnetic resonance imaging agent comprises gadolinium complex of 1,4,7,10-tetraazacyclododecane-1,4,7,10-α,α',α",α'''-tetrakis(methylacetic acid) dimeglumine salt dissolved in physiologically acceptable aqueous solution wherein said salt is present in said solution at a concentration of $1 \times 10^{-5}$ to $1 \times 10$ mol/l.

6. A method of conducting NMR imaging, comprising NMR imaging a patient to whom there has been administered an amount effective to enhance NMR image contrast, of nuclear magnetic resonance imaging agent which comprises gadolinium complex of 1,4,7,10-tetraazacyclododecane-1,4,7,10-α,α',α",α'''-tetrakis(methylacetic acid), or its salt, and a pharmaceutically acceptable inert carrier or diluent.

7. The method of claim 6 wherein the gadolinium complex of 1,4,7,10-tetraazacyclododecane-1,4,7,10-α,α',α", α'''-tetrakis(methylacetic acid) is in its salt form originated from sodium, potassium, lithium, lysine, arginine, ornithine, meglumine or diethanolamine.

8. The method of claim 7 wherein gadolinium complex of 1,4,7,10-tetraazacyclododecane-1,4,7,10-α,α',α",α'''-tetrakis(methylacetic acid) is in its salt form and is dissolved in a physiologically acceptable aqueous solution.

9. The method of claim 8 wherein the gadolinium complex of 1,4,7,10-tetraazacyclododecane-1,4,7,10-α,α',α", α'''-tetrakis(methylacetic acid) is in its salt form and is present in the nuclear magnetic resonance imaging agent in a concentration of $1 \times 10^{-5}$ to $1 \times 10$ mol/l.

10. The method of claim 6 wherein the nuclear magnetic resonance imaging agent comprises gadolinium complex of 1,4,7,10-tetraazacyclododecane-1,4,7,10-α,α',α'',α'''-tetrakis(methylacetic acid) dimeglumine salt dissolved in physiologically acceptable aqueous solution wherein said salt is present in said solution at a concentration of $1 \times 10^{-5}$ to $1 \times 10$ mol/l.

11. A method of imaging body tissue in a patient, comprising subjecting the patient to NMR imaging and prior to performing the NMR imaging, administering to the patient of an amount effective for shortening proton relaxation times in the body tissue undergoing NMR diagnosis, of a nuclear magnetic resonance imaging agent which comprises gadolinium complex of 1,4,7,10-tetraazacyclododecane-1,4,7,10-α,α',α'',α'''-tetrakis(methylacetic acid), or its salt, and a pharmaceutically acceptable inert carrier or diluent.

12. The method of claim 11 wherein the gadolinium complex of 1,4,7,10-tetraazacyclododecane-1,4,7,10-α,α',α'',α'''-tetrakis(methylacetic acid) is in its salt form originated from sodium, potassium, lithium, lysine, arginine, ornithine, meglumine or diethanolamine.

13. The method of claim 12 wherein gadolinium complex of 1,4,7,10-tetraazacyclododecane-1,4,7,10-α,α',α'',α'''-tetrakis(methylacetic acid) is in its salt form and is dissolved in a physiologically acceptable aqueous solution.

14. The method of claim 13 wherein the gadolinium complex of 1,4,7,10-tetraazacyclododecane-1,4,7,10-α,α',α'',α'''-tetrakis(methylacetic acid) is in its salt form and is present in the nuclear magnetic resonance imaging agent in a concentration of $1 \times 10^{-5}$ to $1 \times 10$ mol/l.

15. The method of claim 11 wherein the nuclear magnetic resonance imaging agent comprises gadolinium complex of 1,4,7,10-tetraazacyclododecane-1,4,7,10-α,α',α'',α'''-tetrakis(methylacetic acid) dimeglumine salt dissolved in physiologically acceptable aqueous solution wherein said salt is present in said solution at a concentration of $1 \times 10^{-5}$ to $1 \times 10$ mol/l.

* * * * *

UNITED STATES PATENT AND TRADEMARK OFFICE
CERTIFICATE OF CORRECTION

PATENT NO. : 5,811,077
DATED : September 22, 1998
INVENTOR(S) : Shigemi Seri, et al.

It is certified that error appears in the above-identified patent and that said Letters Patent is hereby corrected as shown below:

On the title page, Item [62], change the filing date of Ser. No. 775,891 from "Oct. 15, 1993" to --Oct. 15, 1991--.

Signed and Sealed this

Twenty-ninth Day of December, 1998

*Attest:*

BRUCE LEHMAN

*Attesting Officer*     *Commissioner of Patents and Trademarks*